United States Patent

Curtis et al.

[11] Patent Number: 4,459,416
[45] Date of Patent: Jul. 10, 1984

[54] WATER SOLUBLE THIOXANTONE PHOTOINITIATORS

[75] Inventors: John R. Curtis, Thanet; Peter E. Heaton, Horwich, both of England

[73] Assignee: Sericol Group Limited, London, England

[21] Appl. No.: 411,570

[22] Filed: Aug. 25, 1982

[30] Foreign Application Priority Data

Nov. 3, 1981 [GB] United Kingdom ............... 8133094

[51] Int. Cl.³ .......................................... C07D 335/16
[52] U.S. Cl. ..................................................... 549/27
[58] Field of Search .......................................... 549/27

[56] References Cited

U.S. PATENT DOCUMENTS 3,642,997 2/1972 Shen et al. ..................... 549/27 X
4,348,530 9/1982 Krita et al. ........................ 549/27
4,385,182 5/1983 Fischer et al. ..................... 549/27

FOREIGN PATENT DOCUMENTS 33720 1/1981 European Pat. Off. .
2050378 1/1981 United Kingdom .
2075506 11/1981 United Kingdom .

Primary Examiner—Richard Raymond
Attorney, Agent, or Firm—Cushman, Darby, Cushman

[57] ABSTRACT

The invention provides novel thioxanthone photoinitiators having the formula:

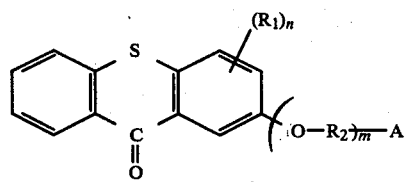

wherein $R_1$ alkyl, alkoxy, alkylthio, halogeno, nitro, amino, alkyl-amino, di-alkyl-amino, hydroxy alkyl-amino, alkanoylamino, benzoylamino, N-alkanoyl-N-benzoyl-amino, sulphonamido, or acetyl, $R_2$ is alkylene, A is —COOH, —SO$_3$H, —OSO$_3$H, or —O—CO—X—COOH (where X is such that HO—CO—X—COOH is a di- or tri-carboxylic acid of up to 8 carbon atoms), n is 0, 1, or 2 and m is 1 or 2, provided that when A is —COOH, m is 2, the aforesaid alkyl, alkoxy, alkanoyl, and alkylene residues containing up to 4 carbon atoms each, as the free acid or as a salt thereof. The photoinitiators may advantageously be used in water-based photopolymerizable compositions, e.g. for use in screen stencil production.

6 Claims, No Drawings

WATER SOLUBLE THIOXANTONE PHOTOINITIATORS

DESCRIPTION

This invention provides novel water-soluble photoinitiators which, when admixed with suitable unsaturated photopolymerisable compounds, can, when irradiated with UV light, produce free radicals which initiate photopolymerisation of the unsaturated photopolymerisable compounds.

The photopolymerisation of unsaturated compounds can be substantially accelerated by a wide variety of initiators, including such compounds as acetophenone, propiophenone, benzophenone, xanthone, thioxanthone, fluorenone, benzaldehyde, anthraquinone, carbazole, thioindigoid dyes and various derivatives of these compounds. Most known initiators however, are unsuitable for use in water-based systems, and, if they are to be used in such systems, require that the initiator be dissolved in a solvent which may or may not be photopolymerisable and dispersed, optionally with further photopolymerisable material, into the aqueous phase to form an emulsion. If the photopolymerisable material present is water-soluble, then the initiator is in a separate phase and cannot work very effectively to bring about photopolymerisation on exposure to actinic light. If, on the other hand, the unsaturated photopolymerisable compounds are in the same (solvent) phase as the initiator, then although photopolymerisation can take place more efficiently, the ability of the photopolymerised material to subsequently insolubilise the ingredients of the aqueous phase and in particular the protective colloid which is normally present is less effective.

In order to produce the most effective insolubilisation of the aqueous phase ingredients by photopolymerisation of the unsaturated compounds, it is preferable for the photopolymerisable unsaturated compounds to be totally or substantially water-soluble and for the initiator also to be water-soluble. When the initiator and unsaturated photopolymerisable material are both fully, or substantially, in the same (aqueous) phase, then photopolymerisation on exposure to UV light can proceed efficiently and the resulting insolubilisation of the aqueous layer ingredients is effective.

For a photoinitiator to work efficiently when exposed to actinic light through glass (as is normally the case when the exposure is carried out with a printing down frame in screen printing), it is highly desirable for it to absorb above 3250° A. However, many simple water soluble photoinitiators do not absorb above this level. Moreover, if the solubilisation of a photoinitiator is attempted by simple sulphonation or inclusion of a carboxy group, the presence of the carboxy or sulpho group on a main benzene ring of the initiator, whether directly attached or separated by a single methylene group, deactivates the molecule and makes it less efficient as a photoinitiator.

Another group of compounds which behave as photoinitiators and are water-soluble are thioindigoid dyes, e.g. the dyestuffs sold under the name "ANTHRASOL" by Farbwerke Hoechst. Several of these are water soluble and capable of photoinitiating the polymerization of unsaturated compounds on exposure to UV light. However, they suffer from the extremely serious drawback that, to remain active, the layer to be photopolymerised must contain moisture. This requires the inclusion of quite large quantities of humectant in the layer which, under conditions of high ambient temperature and humidity can cause reticulation and breakdown problems in the layer.

The water-soluble photoinitiators of the present invention are the thioxanthones of the formula

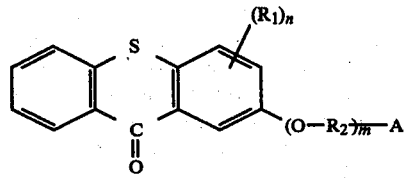

wherein $R_1$ is alkyl, alkoxy, alkylthio, halogeno, nitro, amino, alkyl-amino, di-alkyl-amino, hydroxyalkyl-amino, alkanoylamino, benzoylamino, N-alkanoyl-N-benzoyl-amino, sulphonamido, or acetyl, $R_2$ is alkylene, A is $-COOH$, $-SO_3H$, $-OSO_3H$, or $-O-CO-X-COOH$ (where X is such that $HO-CO-X-COOH$ is a di- or tri-carboxylic acid of up to 8 carbon atoms), n is 0, 1 or 2 and m is 1 or 2, provided that when A is $-COOH$, m is 2, the aforesaid alkyl, alkoxy, alkanoyl, and alkylene residues containing up to 4 carbon atoms each, as the free acid or as a salt thereof. Especially valuable compounds are those in which $R_1$ is methyl, $R_2$ is ethylene, trimethylene, or tetramethylene, A is $-SO_3H$, n is 0, 1 or 2 and m is 1 or 2 as the free acid or as a water-soluble salt thereof.

The aforementioned thioxanthones have the solubilising group separated from the aromatic ring by at least two atoms, which diminishes or eliminates any deactivation effect on the efficiency of the basic photoinitiator molecule. They also absorb strongly around 4000A°, which is very close to one of the main output lines of the mercury lamp units commonly used for exposing photostencil materials, which leads to increased efficacy of the initiator. Moreover, the aforementioned thioxanthones do not require the presence of a humectant and are also much more active than known water-soluble photoinitiators.

Examples of the thioxanthones of the invention which exhibit the aforesaid highly advantageous characteristics are:

2-(2-Sulphoethoxy)-thioxanthone,
2-(3-Sulphopropoxy)-thioxanthone,
2-(2-Sulphoethoxyethoxy)-thioxanthone,
2-(4-Sulphobutoxy)-thioxanthone,
2-(3-Sulphopropoxy)-3-methyl-thioxanthone,
2-(3-Sulphopropoxy)-3-methoxy-thioxanthone,
2-(3-Sulphopropoxy)-3-chloro-thioxanthone,
2-(3-Sulphopropoxy)-3,4-dichloro-thioxanthone, and
2-(3-Sulphopropoxy)-3,4-dimethyl-thioxanthone.

The new thioxanthones are easy to use in water-based photopolymerisable systems and show high reactivity in such systems, especially under the influence of UV light of relatively long wave length. In general they are used in amounts of about 0.1–10%, and preferably 0.5–3%, by weight based on the photopolymerizable ethylenically unsaturated compounds. The most effective UV light for initiating polymerisation has a wavelength from 3500–4500A. Suitable light sources therefore include mercury, xenon, carbon arc, tungsten and some fluorescent lamps.

The unsaturated compounds that can be utilized in such photopolymerizable compositions include: acrylamide, N-methylol-acrylamide, N-vinyl-pyrrolidone, diacetone-acrylamide, hydroxyethyl acrylate, hydroxypropyl acrylate, NN-dimethylamino-ethyl acrylate, NN-diethylaminoethyl acrylate, Uvecryl P101 (UCB), Methylene bis(acrylamide), diethylene glycol diacrylate, triethylene glycol diacrylate, tetraethylene glycol diacrylate, polyethylene glycol 200 diacrylate, and trimethylol propane triacrylate. These unsaturated compounds can be used alone but are usually used as mixtures of such compounds or mixtures in combination with other unsaturated components and the like. The photopolymerisable compositions may also contain other ingredients known for inclusion in such compositions, e.g. additives, pigments, colorants, stabilizers, accelerators, thermal inhibitors, polymer solutions or emulsions, and the like.

The use of the new thioxanthones is described in more detail in our copending Application No. 8133094, filed on even date herewith and entitled "Photopolymerizable materials for use in producing stencils for screen printing", to which reference may be made.

According to a feature of the invention the new thioxanthones are made by reacting a compound of the formula:

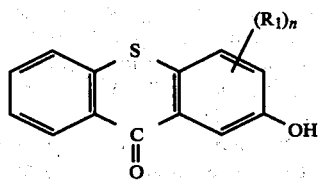

as such or as an alkali metal salt thereof with a compound of the formula:

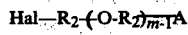

or a salt thereof, where Hal is halogen and $R_1, R_2, n, m$ and A are as hereinbefore defined. This reaction may be effected by heating the reagents together in an appropriate solvent such as dimethylformamide.

The invention is illustrated by the following Examples.

EXAMPLE 1

Concentrated sulphuric acid (300 ml) was slowly added to thiosalicylic acid (30.9 g) and the mixture was stirred for 5 minutes to ensure thorough mixing. Phenol (94 g.) was added slowly to the stirred mixture over a period of 30 minutes. After the addition, the addition was stirred at room temperature for 1 hour, then at 80° C. for two hours, after which it was left to stand at room temperature overnight. The resulting mixture was poured carefully with stirring into 10 times its volume of boiling water which was then boiled for a further 5 mins. The solution was cooled and filtered. The residue was recrystallised from acetone to give 2-hydroxythioxanthone as a yellow product.

2-Hydroxy-thioxanthone (11.40 g) and toluene (125 ml) were mixed and stirred and sodium methoxide (2.97 g) was added thereto portionwise and slowly. The temperature was slowly raised to boiling and the mixture stirred at that temperature for 1 hour. The thioxanthone changed colour from yellow to red indicating conversion to the sodium salt. The reaction mixture was cooled and filtered, and the residue was washed with ether and dried.

1-Chloro-3-bromopropane (104.0 g), ethanol (250 ml), and water (90 ml) were stirred under reflux, and a solution of sodium sulphite (25.0 g) in distilled water (90 ml) was added to the stirred refluxing reaction mixture over a period of two hours. After the addition, refluxing was continued for a further 2 hours after which the excess alcohol and 1-chloro-3-bromopropane were removed by distillation. The remaining aqueous solution was evaporated to dryness on a steam bath and the product was recrystallised from alcohol to yield sodium 3-chloro-propane-sulphonate as a white crystalline solid.

The salt of 2-hydroxy-thioxanthone (8.6 g), sodium 3-chloro-propane-sulphonate (6.6 g) and dimethyl formamide (150 ml) were stirred under reflux for 2 hours. The resulting mixture was cooled and poured into a large excess of acetone. The solid was collected and recrystallised from methanol to give the sodium salt of 2-(3-sulphopropoxy)thioxanthone.

EXAMPLE 2

Bis(2-chloroethyl)ether (94.4 g), ethanol (250 ml) and water (90 ml) were stirred together under reflux, and a solution of sodium sulphite (25.0 g) in distilled water (90 ml) was added to the stirred, refluxing reaction mixture over a period of 2 hours. After the addition, refluxing was continued for two hours after which time the excess alcohol and bis(2-chloroethyl) ether were removed by distillation. The remaining aqueous solution was evaporated to dryness on a water bath to give a white crystalline solid, which was stirred with diethyl ether and filtered to yield sodium 2-chloroethoxyethyl sulphonate.

The sodium salt of 2-hydroxythioxanthone (22.5 g), sodium 2-chloroethoxyethyl-sulphonate (20.8 g), and dimethyl formamide (250 ml) were stirred together under reflux for 1 hour. The resulting mixture was cooled and poured into a large excess of acetone. The yellow precipitate was filtered off and recrystallised from boiling methanol to give the sodium salt of 2-(2-sulphoethoxyethoxy)thioxanthone.

EXAMPLE 3

1,4-Dibromo-butane (142.5 g), ethanol (250 ml) and water (90 ml) were stirred together under reflux. A solution of sodium sulphite (25.0 g) and distilled water (90 ml) was added to the stirred, refluxing reaction mixture over a period of two hours. After the addition, refluxing was continued for two hours, after which the excess ethanol and 1,4-dibromobutane were removed by distillation. The remaining aqueous solution was evaporated to dryness on the steam bath, and the residue was slurried with ether, filtered and dried to give sodium 4-bromo-butane sulphonate.

Sodium 4-bromobutane sulphonate (15.5 g), the sodium salt of 2-hydroxythioxanthone (15.0 g) and dimethyl-formamide (200 ml) were stirred under reflux for two hours. The resulting mixture was cooled and poured with stirring into 600 ml of acetone. The precipitated solid was collected by filtration and recrystallised from boiling methanol to give the sodium salt of 2-(4-sulphobutoxy)thioxanthone.

EXAMPLE 4

Concentrated sulphuric acid (300 ml) was slowly added to thiosalicylic acid (30.9 g) and the mixture was stirred for 5 minutes to ensure thorough mixing. To the stirred mixture was added slowly over a period of 30 minutes 2,3-dimethyl-phenol (138 g). After the addition, the mixture was stirred at room temperature for 1 hour, and then at 80° C. for 2 hours, after which it was left to stand at room temperature overnight. The resulting mixture was poured carefully with stirring into 10 times its volume of boiling water after which it was boiled for a further five minutes, cooled, and filtered. The residue was recrystallised from acetone to give 2-hydroxy-3,4-dimethyl-thioxanthone as a yellow product.

2-Hydroxy-3,4-dimethyl-thioxanthone (10.2 g), and 5M sodium hydroxide solution (150 ml) were stirred and heated together until the yellow colour had completely changed to red. The reaction mixture was cooled and filtered. The residue was washed with acetone and dried to give the sodium salt of 2-hydroxy-3,4-dimethyl-thioxanthone.

The sodium salt of 2-hydroxy-3,4-dimethyl-thioxanthone (6.5 g), sodium 3-chloro-propane-sulphonate (4.3 g) and dimethyl-formamide (150 ml) were stirred under reflux for 4 hours. The resulting mixture was cooled and poured into a large excess of acetone. The solid was separated and recrystallised from methanol to give the sodium salt of 2-(3-sulphopropoxy)-3,4-dimethyl-thioxanthone.

The thioxanthones of the present invention may, for example, be used as follows.

EXAMPLE 5

A photosensitive coating composition of the following formula was made up:

| | |
|---|---|
| 13% Aqueous solution of Gohsenol GM20 (polyvinyl alcohol of Nippon Gohsei) | 50.0 |
| Methylene bis-acrylamide | 0.5 |
| Acrylamide | 5.0 |
| Methyl diethanolamine | 1.0 |
| 2-(3-Sulphopropoxy)-thioxanthone | 0.1 |
| 50% Irgalite Blue CPV2 Paste* (Ciba-Geigy) | 0.1 |

This composition was coated on to a suitable (top coated) polyester film substrate, and dried. The resulting layer was exposed via a positive transparency to a 800 W mercury halide lamp at a distance of 1 meter for 10 seconds. After development with water to remove the water-soluble unexposed areas, a good, visible relief image was obtained.

We claim:

1. A thioxanthone of the formula:

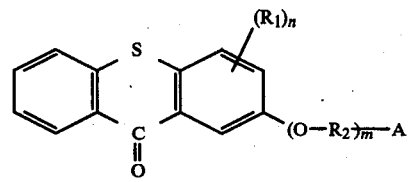

wherein $R_1$ is alkyl, alkoxy, alkylthio, halogeno, nitro, amino, alkyl-amino, di-alkyl-amino, hydroxy alkyl-amino, alkanoylamino, benzoylamino, N-alkanoyl-N-benzoyl-amino, or acetyl, $R_2$ is alkylene, A is —COOH, —SO$_3$H, —OSO$_3$H, or —O—CO—X—COOH (where X is such that HO—CO—X—COOH is a di- or tri-carboxylic acid of up to 8 carbon atoms), n is 0, 1 or 2 and m is 1 or 2, provided that when A is —COOH, m is 2, the aforesaid alkyl, alkoxy, alkanoyl, and alkylene residues containing up to 4 carbon atoms each, as the free acid or as a salt thereof.

2. A thioxanthone according to claim 1 wherein $R_1$ is methyl, $R_2$ is ethylene, trimethylene, or tetramethylene, A is —SO$_3$H, n is 0, 1 or 2 and m is 1 or 2 as the free acid or as a water-soluble salt thereof.

3. A thioxanthone according to claim 1 which is 2-(3-sulphopropoxy)thioxanthone or a water-soluble salt thereof.

4. A thioxanthone according to claim 1 which is 2-[2-(2-sulphoethoxy)ethoxy]thioxanthone or a water-soluble salt thereof.

5. A thioxanthone according to claim 1 which is 2-(4-sulphobutoxy)thioxanthone or a water-soluble salt thereof.

6. A thioxanthone according to claim 1 which is 2-(3-sulphopropoxy)-3,4-dimethyl-thioxanthone or a water-soluble salt thereof.

* * * * *